(12) United States Patent
Matsumoto et al.

(10) Patent No.: US 7,897,787 B2
(45) Date of Patent: Mar. 1, 2011

(54) MALEIMIDE DERIVATIVE

(75) Inventors: Takuya Matsumoto, Tokyo (JP); Takuji Shoda, Chiba (JP); Yasuteru Urano, Kanagawa (JP); Tetsuo Nagano, Tokyo (JP)

(73) Assignee: The University of Tokyo, Tokyo (JP)

( * ) Notice: Subject to any disclaimer, the term of this patent is extended or adjusted under 35 U.S.C. 154(b) by 37 days.

(21) Appl. No.: 12/066,323

(22) PCT Filed: Sep. 13, 2006

(86) PCT No.: PCT/JP2006/318104

§ 371 (c)(1),
(2), (4) Date: Jul. 13, 2009

(87) PCT Pub. No.: WO2007/032363

PCT Pub. Date: Mar. 22, 2007

(65) Prior Publication Data
US 2009/0318707 A1     Dec. 24, 2009

(30) Foreign Application Priority Data
Sep. 13, 2005     (JP) ............................. 2005-264776

(51) Int. Cl.
*C07F 5/02* (2006.01)
(52) U.S. Cl. .................. 548/405; 548/410; 540/468; 540/469
(58) Field of Classification Search ............ 548/405, 548/410; 540/468, 469
See application file for complete search history.

(56) References Cited

U.S. PATENT DOCUMENTS

| | | | |
|---|---|---|---|
| 5,981,746 A | 11/1999 | Wolfbeis et al. | |
| 6,001,999 A * | 12/1999 | Wolfbeis et al. | ............ 540/468 |
| 6,171,520 B1 | 1/2001 | Imai et al. | |
| 2004/0147728 A1 | 7/2004 | Meltola et al. | |
| 2004/0157231 A1 | 8/2004 | Meltola et al. | |

FOREIGN PATENT DOCUMENTS

JP     10338695     12/1998
JP     11005796     1/1999

* cited by examiner

*Primary Examiner*—Yong Chu
(74) *Attorney, Agent, or Firm*—Greenblum & Bernstein, P.L.C.

(57) ABSTRACT

A compound represented by the following general formula (I):

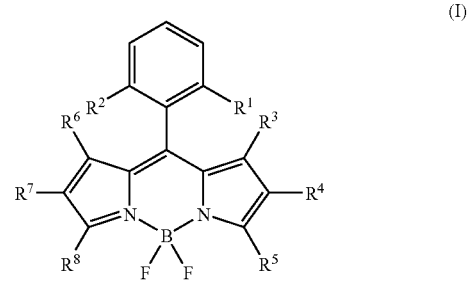

[wherein $R^1$ and $R^2$ independently represent hydrogen atom, or a group represented by the following formula (A):

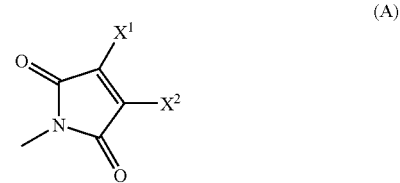

(wherein $X^1$ and $X^2$ represent hydrogen atom, an alkyl group, an alkoxy group, or a halogen atom), provided that $R^1$ and $R^2$ do not simultaneously represent hydrogen atom; $R^3$ and $R^6$ represent an alkyl group; $R^4$ and $R^7$ represent hydrogen atom, an alkyl group, carboxy group, an alkoxycarbonyl group, or sulfo group; and $R^5$ and $R^8$ represents an alkyl group, an aryl group, an alkoxycarbonyl group, a vinyl group, a thienyl group, or a pyrrolyl group], or a salt thereof, which is usable for efficient screening for a chemical substance having applicability as a catalyst of the reaction of Michael addition.

5 Claims, 5 Drawing Sheets

MALEIMIDE DERIVATIVE

TECHNICAL FIELD

The present invention relates to a novel maleimide derivative. More specifically, the present invention relates a maleimide derivative having a property that the derivative, per se, is substantially non-fluorescent, whilst emits intense fluorescence after reaction with a nucleophilic agent.

BACKGROUND ART

One of major objects of researches in organic chemistry is to create highly efficient chemical catalysts. In development of catalysts, besides determination of whether a test substance functions as a highly active catalyst, it is essential to optimize reaction conditions. Conventionally for developing catalysts, a means has been used in which advance of a catalytic reaction is monitored over period of time by high performance liquid chromatography or the like. However, a huge number of chemical substances are created due to recent progress of combinatorial techniques, and as a result, it has become difficult to conduct a screening for chemical substances having applicability as catalysts by applying the conventional means. Moreover, even if chemical substances having applicability as catalysts are chosen, it is still impossible to efficiently perform development of catalysts including optimization of reaction conditions by using the conventional means. From such viewpoints, it has been desired to provide a means that enables efficient screening for chemical substances having applicability as catalysts and convenient selection of optimum reaction conditions in a short time.

The reaction of Michael addition is widely used in the field of organic synthesis as a fundamental carbon-carbon bond formation reaction, and it is desired to develop a system capable of efficiently advancing the reaction of Michael addition. If efficient screening for catalytic substances used in the reaction of Michael addition and efficient determination of conditions for the reaction system are achieved, it is expected that the development of the reaction system of Michael addition, which is currently carried out for every test substance on trial and error basis, can be remarkably progressed.

Direct fluorescence visualization of intracellular localizations and dynamic behaviors of proteins in living cells and tissues is extremely important for elucidation of physiological functions of the proteins, and techniques using a protein fused with GFP (Green Fluorescent Protein) are widely used in recent years. However, behavior of a target protein may possibly not be correctly monitored with GFP due to a problem concerning a molecular size or the like of GFP itself. Accordingly, a means has been desired for achieving specific and highly sensitive fluorescence visualization of a target protein based on introduction of a fluorescence tag having a smaller molecular size. The inventors of the present invention found that a compound having 7-hydroxycoumarin as a fluorophore and two maleimide groups reacted with a peptide having two adjacent cysteine residues in the same molecule, and revealed that the compound was substantially non-fluorescent before the reaction, whilst it came to emit intense fluorescence after the reaction, and thereby the compound was useful as a technique for introducing a fluorescence tag into a peptide (Abstract of Photochemistry Symposium, Sep. 12 to 14, 2005). However, excitation wavelength of the aforementioned compound having 7-hydroxycoumarin and two maleimide groups is in the ultraviolet region, and accordingly the compound may sometimes causes a problem of cytotoxicity. Moreover, from a viewpoint of application to a biological system, improvement of reaction selectivity to a peptide having two adjacent cysteine residues in a molecule was another object. Therefore, it has been desired to develop a technique for highly selective introduction of a fluorescence tag into a protein, and for excitation with a visible light that is free from cytotoxicity with excitation.

DISCLOSURE OF THE INVENTION

Object to be Achieved by the Invention

An object of the present invention is to provide a means for efficient screening of chemical substances having applicability as catalysts in the reaction of Michael addition, and convenient selection of optimum reaction conditions in a short time. More specifically, the object of the present invention is to provide a novel chemical substance which is a compound having a property of inducing the reaction of Michael addition by a reaction with a nucleophilic agent, and also having a property that the compound per se is substantially non-fluorescent and gives a fluorescent chemical substance as a product of the reaction of Michael addition. Another object of the present invention is to provide a means capable of highly selectively introducing a fluorescence tag which can be excited with a visible light that causes no cell injury by excitation, into a protein.

Means for Achieving the Object

The inventors of the present invention conducted various researches to achieve the aforementioned objects. As a result, on the basis of combination of a fluorescence chromophore of an indacene derivative having an ion uptaking moiety useful for alkali metal ion or cation measurement (Japanese Patent Laid-Open Publication (KOKAI) Nos. 10-338695 and 11-5796) and maleimide group, they succeeded in providing a compound having properties of being per se substantially non-fluorescent and providing a highly fluorescent Michael adduct after reaction with a nucleophilic agent. For example, when the aforementioned compound and a nucleophilic agent are reacted in the presence of a test substance of which applicability as a catalyst is to be determined, and a fluorescent Michael adduct is quantified on the basis of fluorescence intensity, it can be determined whether the test substance can be used as a catalyst of the reaction of Michael addition. Further, by preparing reaction systems of various solvents, temperatures and the like to quantify a Michael adduct obtained after the reaction, an optimum reaction system can be conveniently chosen. They also found that the aforementioned compound had a property of easily reacting with thiol group of a compound having the thiol group in a molecule (for example, thiol group of cysteine) to change into a fluorescent substance, thereby said compound can be used for labeling of a peptide (oligopeptide or polypeptide) or a protein having a cysteine residue. The present invention was accomplished on the basis of the aforementioned findings.

The present invention thus provides a compound represented by the following general formula (I):

[Formula 1]

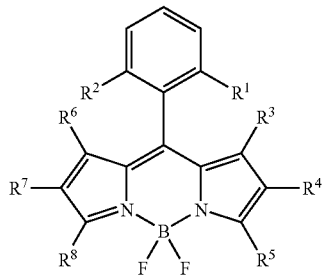

[wherein $R^1$ and $R^2$ independently represent hydrogen atom, or a group represented by the following formula (A):

[Formula 2]

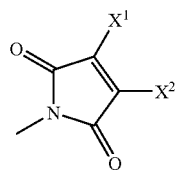

(wherein $X^1$ and $X^2$ independently represent hydrogen atom, a $C_{1-6}$ alkyl group which may have a substituent, a $C_{1-6}$ alkoxy group which may have a substituent, or a halogen atom), provided that $R^1$ and $R^2$ do not simultaneously represent hydrogen atom; $R^3$ and $R^6$ independently represent a $C_{1-6}$ alkyl group which may have a substituent; $R^4$ and $R^7$ independently represent hydrogen atom, a $C_{1-6}$ alkyl group which may have a substituent, carboxy group, a $C_{1-6}$ alkoxycarbonyl group, or sulfo group, or $R^4$ may combine with $R^3$ to form a condensed aryl ring together with two carbon atoms to which they bond (the aryl ring may have a substituent), and/or $R^7$ may combine with $R^6$ to form a condensed aryl ring together with two carbon atoms to which they bond (the aryl ring may have a substituent); and $R^5$ and $R^8$ independently represent a $C_{1-6}$ alkyl group which may have a substituent, an aryl group which may have a substituent, a $C_{1-6}$ alkoxycarbonyl group which may have a substituent, a vinyl group which may have a substituent, a thienyl group which may have a substituent, or a pyrrolyl group which may have a substituent], or a salt thereof.

The aforementioned compound or a salt thereof has a property of being per se substantially non-fluorescent, and providing a highly fluorescent Michael adduct after reaction with a nucleophilic agent.

According to a preferred embodiment of the aforementioned invention, there is provided the aforementioned compound or a salt thereof, wherein $R^1$ is a group represented by the formula (A), $R^2$ is hydrogen atom, and $X^1$ and $X^2$ are hydrogen atoms.

From another aspect, there is provided the aforementioned compound or a salt thereof, which is for use in search for a reaction system of Michael addition. The search for the reaction system includes screening for a substance having applicability as a catalyst, as well as selection of reaction conditions such as solvent and/or reaction temperature, and the like. Typically, to a reaction system in a state of solution containing the aforementioned compound or a salt thereof and a nucleophilic agent, a test substance which is to be determined whether to have applicability as a catalyst of the reaction of Michael addition is added, and then monitoring intensity of fluorescence emitted from a Michael adduct produced as a product of the reaction of Michael addition to determine advance of the reaction of Michael addition enables determination of whether or not the test substance functions as a catalyst for Michael reaction. In another typical example, by adding a catalyst of the reaction of Michael addition to a reaction system containing the aforementioned compound or a salt thereof, a nucleophilic agent, and one or more kinds of solvents, and then monitoring intensity of fluorescence emitted from a Michael adduct to determine advance of the reaction of Michael addition, it can be determined whether or not the solvent(s) give(s) a reaction system suitable for the combination with the catalyst. By performing the aforementioned reaction at several kinds of temperatures, optimum reaction temperature can also be chosen.

From a still further aspect, there is provided the aforementioned compound or a salt thereof, which is used for labeling of a peptide, an oligopeptide, a polypeptide, or a protein each of which has a cysteine residue. The aforementioned compound or a salt thereof induces the reaction of Michael addition with thiol group of a cysteine residue to give a highly fluorescent Michael adduct. As a result, a peptide, a protein or the like labeled with the fluorescent Michael adduct can be easily obtained. When both $R^1$ and $R^2$ are the groups represented by the formula (A), a Michael adduct in which either $R^1$ or $R^2$ causes the reaction of Michael addition is substantially non-fluorescent, and only a Michael adduct in which both $R^1$ and $R^2$ cause the reaction of Michael addition gives intense fluorescence. As a result, only a peptide, a protein, or the like having two adjacent cysteine residues in the same molecule can be recognized at multiple points, and thus selectively labeled with fluorescence.

BEST MODE FOR CARRYING OUT THE INVENTION

Figure 1:
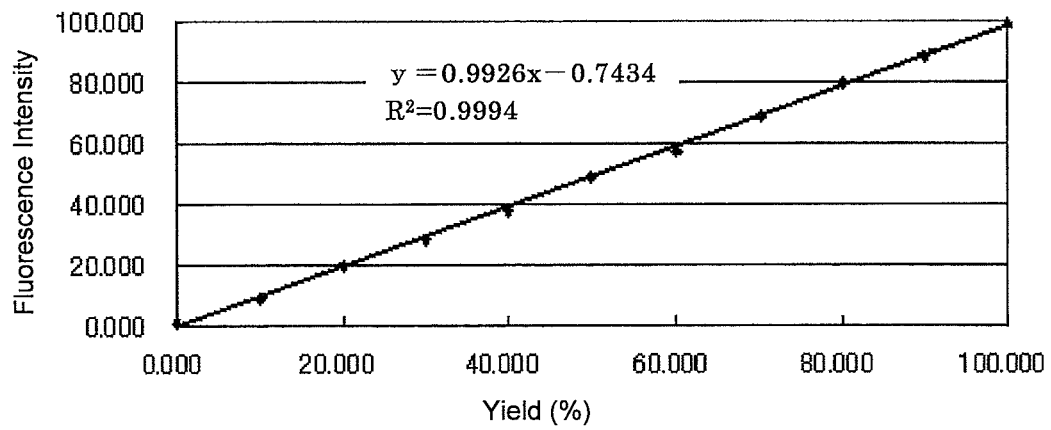
FIG. 1 Graph showing a calibration curve for performing high throughput screening for catalysts and solvents for the reaction of Michael addition (Examples 5 and 7).

In this specification, the alkyl moiety of the "alkyl group" or the substituents having an alkyl moiety (for example, alkoxy group and the like) means a saturated hydrocarbon group consisting of a linear chain, a branched chain, a cyclic chain, or a combination thereof. More specifically, examples of the alkyl group include methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like.

In this specification, when a certain functional group is referred to with the expression "which may have a substituent", type, number and substitution position of the substituent are not particularly limited, and it may have, for example, an alkyl group, a halogen atom (any of fluorine atom, chlorine atom, bromine atom and iodine atom), hydroxy group, amino group, carboxy group, sulfo group, an alkylsulfonate group, or the like as the substituent. Further, although the aryl group referred to in this specification may be either a monocyclic or polycyclic aryl group, phenyl group can be preferably used. The same shall apply to the aryl ring, and a benzene ring can be preferably used.

In the compound represented by the aforementioned general formula (I), it is preferred that either one of $R^1$ and $R^2$ is hydrogen atom, and the other is a group represented by the formula (A), and it is also preferred that both $R^1$ and $R^2$ are groups represented by the formula (A). In the latter case, when the compound or a salt thereof of the present invention is used as labeling agent for a peptide, protein, or the like, each of adjacent thiol groups of two cysteine residues react respectively with each of two groups represented by the formula (A), fluorescence emission occurs only in a Michael adduct in which both $R^1$ and $R^2$ have reacted, and therefore a peptide, protein or the like having two adjacent cysteine residues can be selectively labeled with fluorescence by using the compound of the present invention.

As the $C_{1-6}$ alkyl group represented by $R^4$ or $R^7$, methyl group, ethyl group and the like are preferred, and as the $C_{1-6}$ alkoxycarbonyl group (in this specification, "$C_{1-6}$ alkoxycarbonyl group" means a carbonyl group substituted with a $C_{1-6}$ alkoxy), ethoxycarbonyl group and the like are preferred. When $R^4$ combines with $R^3$ to form a condensed aryl ring, and when $R^7$ combines with $R^6$ to form a condensed aryl ring, benzene ring is preferred as the aryl ring to be formed. When $R^4$ and $R^7$ are groups other than hydrogen atom, fluorescence wavelength of the compound may shift to a long wavelength side, and water solubility thereof may increase.

Examples of the substituted $C_{1-6}$ alkyl group represented by $R^4$ or $R^7$ include, for example, a carboxy-substituted $C_{1-6}$ alkyl group, an alkoxycarbonyl-substituted $C_{1-6}$ alkyl group, a sulfo-substituted $C_{1-6}$ alkyl group, an alkylsulfonate-substituted $C_{1-6}$ alkyl group, and the like. The carboxy-substituted $C_{1-6}$ alkyl group is preferably a monocarboxy-substituted $C_{1-6}$ alkyl group. Examples of the alkoxycarbonyl-substituted $C_{1-6}$ alkyl group include $C_{1-6}$ alkyl esters of the aforementioned carboxy-substituted $C_{1-6}$ alkyl group. As the sulfo-substituted $C_{1-6}$ alkyl group, monosulfo-substituted $C_{1-6}$ alkyl group is preferred. As the alkylsulfonate-substituted $C_{1-6}$ alkyl group, a monoalkylsulfonate-substituted $C_{1-6}$ alkyl group is preferred. As the alkylsulfonate group in the alkylsulfonate-substituted $C_{1-6}$ alkyl group, a $C_{1-6}$ alkylsulfonate ($C_{1-6}$ alkyl-O—$SO_2$—) is preferred.

The $C_{1-6}$ alkyl group and the substituted $C_{1-6}$ alkyl group represented by $R^5$ or $R^8$ are the same as those mentioned above. As the aryl group represented by $R^5$ or $R^8$, a phenyl group is preferred. When the phenyl group has a substituent, as the substituent, sulfo group or a sulfonate group is preferred, and sulfo group is particularly preferred. As the $C_{1-6}$ alkoxycarbonyl group represented by $R^5$ or $R^8$, ethoxycarbonyl group is preferred. Examples of the substituent existing on the vinyl group represented by $R^5$ or $R^8$ include phenyl group, a monoaminophenyl group, a diaminophenyl group (for example, 3,4-diaminophenyl group), and the like. As the thienyl group or pyrrolyl group represented by $R^5$ or $R^8$, 2-thienyl group or 2-pyrrolyl group is preferred, respectively. When $R^5$ and $R^8$ are groups other than alkyl group, fluorescence wavelength of the compound may shift to a long wavelength side.

As the substituents represented by $X^1$ and $X^2$ in the aforementioned formula (A), any kind of substituent may be chosen unless the substituent inhibits the reaction of Michael addition of the compound of the present invention represented by the aforementioned general formula (I) with a nucleophilic agent. Examples include hydrogen atom, a $C_{1-6}$ alkyl group which may have a substituent, a $C_{1-6}$ alkoxy group which may have a substituent, a halogen atom, and the like.

The compound of the present invention represented by the aforementioned general formula (I) can exist as an acid addition salt or a base addition salt. Examples of the acid addition salt include mineral acid salts such as hydrochlorides, sulfates and nitrates, organic acid salts such as methanesulfonates, p-toluenesulfonates, oxalates, citrates and tartrates, and the like, and examples of the base addition salt include metal salts such as sodium salts, potassium salts, calcium salts and magnesium salts, ammonium salts, organic amine salts such as triethylamine salts, and the like. In addition to the above examples, the compound may form a salt with an amino acid such as glycine. The compound or a salt thereof of the present invention may exist as a hydrate or a solvate, and any of these substances fall within the scope of the present invention.

The compound of the present invention represented by the aforementioned general formula (I) may have one or two or more asymmetric carbons depending on types of substituents. Stereoisomers such as optical isomers based on one or more asymmetric carbons and diastereoisomers based on two or more asymmetric carbons, as well as arbitrary mixtures of stereoisomers, racemic compounds, and the like fall within the scope of the present invention.

Methods for preparing typical examples of the compound of the present invention are specifically shown in the examples of this specification. Therefore, those skilled in the art can prepare any of the compounds of the present invention represented by the aforementioned general formula (I) by suitably choosing reaction raw materials, reaction conditions, reagents, and the like on the basis of those explanations, and adding modification or alteration to those methods as required. Synthetic methods of the indacene structure are mentioned in, for example, Japanese Patent Laid-Open Publication Nos. 10-338695 and 11-5796; New J. Chem., 25, pp. 289-292, 2001; Tetrahedron Letters, 42, pp. 6711-6713, 2001; Angew. Chem. Int. Ed., 40, pp. 385-387, 2001; Japanese Patent Laid-Open Publication No. 2003-277385, and the like, and therefore, by referring to these publications, those skilled in the art can prepare the compound of the present invention still more easily. The entire disclosures of the aforementioned publications are incorporated in the disclosure of the specification as reference.

The compound represented by the aforementioned general formula (I) or a salt thereof has a property that it exists as a substance which is substantially non-fluorescent per se, whilst it easily reacts with a nucleophilic agent to give a Michael adduct which emits intense fluorescence. By using this property, the compound or a salt thereof of the present invention can be used for search for a reaction system of the reaction of Michael addition. The search for a reaction system includes, besides screening for substances having applicability as a catalyst, selection of reaction conditions such as solvent and/or reaction temperature, selection of a combination of two or more reaction conditions selected from the group consisting of starting compound, reagent, catalyst, solvent, reaction temperature, and the like, and the term "search for a reaction system" should not be construed in any limitative way in any sense.

Typically, the compound or a salt thereof of the present invention can be used for a method comprising adding a test substance, which is to be determined whether to have applicability as a catalyst of the reaction of Michael addition, to a reaction system containing the aforementioned compound or a salt thereof and a nucleophilic agent in a state of solution, and measuring intensity of fluorescence emitted by a Michael adduct to confirm production of the Michael adduct as a product of the reaction of Michael addition and thereby determine that the test substance has the catalytic activity; a method comprising monitoring intensity of fluorescence emitted by a Michael adduct to determine advance of the reaction of Michael addition with similar steps to the above, and thereby determine whether the test substance efficiently functions as a catalyst of the reaction of Michael addition, and the like. In another typical example, by adding a catalyst of the reaction of Michael addition to a reaction system containing the aforementioned compound or a salt thereof, a nucleophilic agent and one or more kinds of solvents, and monitoring intensity of fluorescence emitted by a Michael adduct to determine advance of the reaction of Michael addition, it can be determined whether the solvent(s) give(s) a suitable reaction system in combination with the catalyst. Moreover, by performing the aforementioned reaction at several temperatures, optimum reaction temperature can also be chosen. However, the searching methods of the reaction system specifically explained above are given solely for exemplification, and embodiments of using the compound or a salt thereof of the present invention are not limited to the applications in the aforementioned methods.

Further, the compound represented by the aforementioned general formula (I) or a salt thereof has a property that it exists as a substance which per se is substantially non-fluorescent, whilst it efficiently reacts with thiol group of a cysteine residue to give a Michael adduct. The resulting Michael adduct has a property of emitting intense fluorescence as explained above, and therefore, an amino acid, a peptide (an oligopeptide, a polypeptide), a protein or the like having a cysteine residue can be labeled with fluorescence by using the compound or a salt thereof of the present invention. Therefore, the compound or a salt thereof of the present invention is useful as a fluorescence-labeling agent for biological substances having a cysteine residue.

EXAMPLES

Hereafter, the present invention will be explained more specifically with reference to examples. However, the scope of the present invention is not limited to the following examples.

Example 1

Synthesis of Compound 4

The synthetic scheme of Compound 4 is shown below.

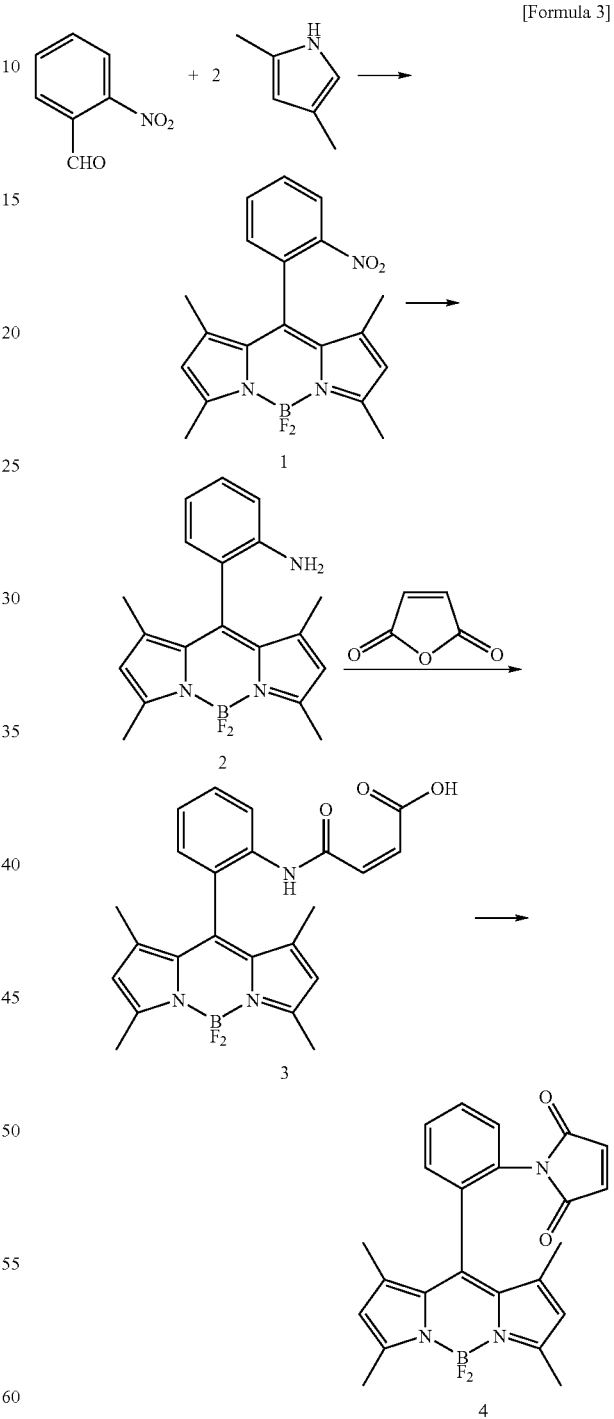

[Formula 3]

(a) Synthesis of Compound 1

2-Nitrobenzaldehyde (0.61 g, 4.0 mmol) and 2,4-dimethylpyrrole (0.76 g, 8.0 mmol) were dissolved in 350 mL of dichloromethane. The solution was added with several drops of trifluoroacetic acid under an argon atmosphere, and the mixture was stirred overnight at room temperature with light shielding. Disappearance of the starting materials was confirmed by thin layer chromatography (developing solvent: dichloromethane, alumina), and then the reaction mixture was added with 150 mL of a solution of DDQ (2,3-dichloro-5,6-dicyanobenzoquinone, 0.91 g, 4.0 mmol) in dichloromethane. The reaction mixture was stirred at room temperature for 20 minutes, and then washed three times with water and once with saturated brine. The washed aqueous layer was extracted with dichloromethane, and the dichloromethane layer was combined with the original dichloromethane layer and dried over anhydrous magnesium sulfate. The organic layer was concentrated under reduced pressure, and the residue was purified by alumina column chromatography (eluent: dichloromethane). The resulting brown solid was dissolved in 200 mL of toluene, the solution was added with 5 mL of DIEA (diisopropylethylamine), and further added with 5 mL of $BF_3$—$OEt_2$ (boron trifluoride-diethyl ether complex) under an argon atmosphere, and the mixture was stirred at room temperature for 30 minutes. After completion of the reaction, the reaction mixture was washed three times with water and once with saturated brine. The aqueous layer was extracted with ethyl acetate once, and all the organic layers were combined, and dried over anhydrous sodium sulfate. The organic layer was concentrated under reduced pressure, and then the residue was purified by silica gel column chromatography (eluent: n-hexane/dichloromethane=1/1) to obtain Compound 1 as red solid (0.9 g, yield: 61%).

$^1$H-NMR (300 MHz, $CDCl_3$) δ 1.36 (6H, s), 2.56 (6H, s), 5.99 (2H, s), 7.47 (1H, d, J=7.5 Hz), 7.70 (1H, t, J=7.5 Hz), 7.79 (1H, t, J=7.5 Hz), 8.19 (1H, d, J=7.5 Hz).

MS (EI+) 369 [M]+.

Anal. Calcd for $C_{19}H_{18}BF_2N_3O_2$, C, 61.81%; H, 4.91%; N, 11.38% Found, C, 61.87%; H, 5.13%; N, 11.41%.

(b) Synthesis of Compound 2

Compound 1 (0.7 g, 1.9 mmol) was dissolved in 50 mL of dichloromethane, and the solution was added with 250 mL methanol. The mixture was added with 10% Pd/C (20 mg), and stirred overnight at room temperature under a hydrogen atmosphere with light shielding. After disappearance of the starting materials was confirmed by thin layer chromatography (developing solvent: dichloromethane, silica gel), 10% Pd/C was removed by filtration. The reaction mixture was concentrated under reduced pressure, and then the residue was purified by silica gel column chromatography (eluent: dichloromethane) to obtain Compound 2 as orange solid (93 mg, yield: 14%).

$^1$H-NMR (300 MHz, $CDCl_3$) δ 1.55 (6H, s), 2.56 (6H, s), 3.73 (2H, s), 5.99 (2H, s), 6.75 (1H, d, J=7.5 Hz), 6.87 (1H, t, J=7.5 Hz), 7.00 (1H, dd, J=7.5, 1.4 Hz), 7.23 (1H, dd, J=7.5, 1.4 Hz).

MS (EI+) 339 [M]+.

(c) Synthesis of Compound 3

Compound 2 (546 mg, 1.6 mmol) and maleic anhydride (188 mg, 1.9 mmol) were dissolved in 200 mL of acetic acid, and the solution was stirred at room temperature for 3 hours and 30 minutes with light shielding. After disappearance of the starting materials was confirmed by thin layer chromatography (developing solvent: dichloromethane/methanol=19/1, silica gel), the reaction mixture was concentrated under reduced pressure. The residue was purified by silica gel column chromatography (eluent: dichloromethane/methanol=19/1) to obtain Compound 3 as orange solid (761 mg, yield: quantitative).

$^1$H-NMR (300 MHz, $CDCl_3$) δ 1.42 (6H, s), 2.54 (6H, s), 6.02 (2H, s), 6.25 (1H, d, J=13.0 Hz), 6.35 (1H, d, J=13.0 Hz), 7.29 (1H, dd, J=8.0 Hz, 1.7 Hz), 7.40 (1H, td, J=8.0, 1.7 Hz), 7.58 (1H, td, J=8.0 Hz, 1.7 Hz), 8.23 (1H, br), 8.33 (1H, dd, J=1.7 Hz, 8.0 Hz).

MS (ESI+) 460, [M+Na]+.

(d) Synthesis of Compound 4

Compound 3 (672 mg, 1.5 mmol) and sodium acetate (139 mg, 1.7 mmol) were added with 200 mL of acetic anhydride, and the mixture was stirred overnight at 80° C. with light shielding. After disappearance of the starting materials was confirmed by thin layer chromatography (developing solvent: dichloromethane/methanol=19/1, silica gel), the reaction mixture was concentrated under reduced pressure. The residue was dissolved in dichloromethane, and the dichloromethane layer was washed three times with water and once with saturated brine. The aqueous layer was extracted with dichloromethane, and the dichloromethane layer was combined with the original dichloromethane layer, and dried over anhydrous magnesium sulfate. The organic layer was concentrated under reduced pressure, and then the residue was purified by silica gel column chromatography (eluent: dichloromethane) to obtain Compound 4 as orange solid (483 mg, yield: 75%).

Melting point: 257.8-258.3° C.

$^1$H-NMR (300 MHz, $CDCl_3$) δ 1.57 (6H, s), 2.50 (6H, s), 5.96 (2H, s), 6.64 (2H, s), 7.32-7.39 (1H, m), 7.45-7.51 (1H, m), 7.57-7.65 (2H, m).

$^{13}$C-NMR (75 MHz, $CDCl_3$) δ 14.5, 14.7, 121.4, 129.8, 130.2, 130.5, 130.8, 130.9, 131.1, 134.0, 135.0, 136.5, 143.9, 155.9, 169.4

HRMS (ESI+) Calcd for [M+Na]+, 442.1514, Found: 442.1518

IR (KBr, cm$^{-1}$) 478, 686, 716, 831, 980, 1084, 1157, 1194, 1306, 1389, 1508, 1543, 1719

Anal. Calcd for $C_{23}H_{20}F_2N_3O_2$, C, 65.89%; H, 4.81%; N, 10.02% Found, C, 65.79%; H, 4.94%; N, 9.94%.

Example 2

Synthesis of Compound 7

The synthesis scheme of Compound 7 is shown below.

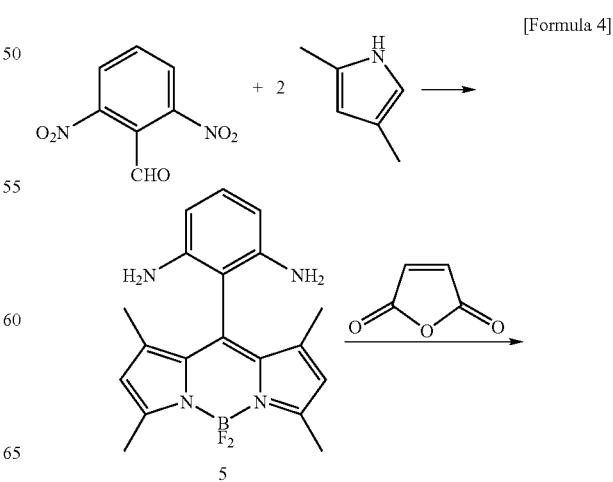

[Formula 4]

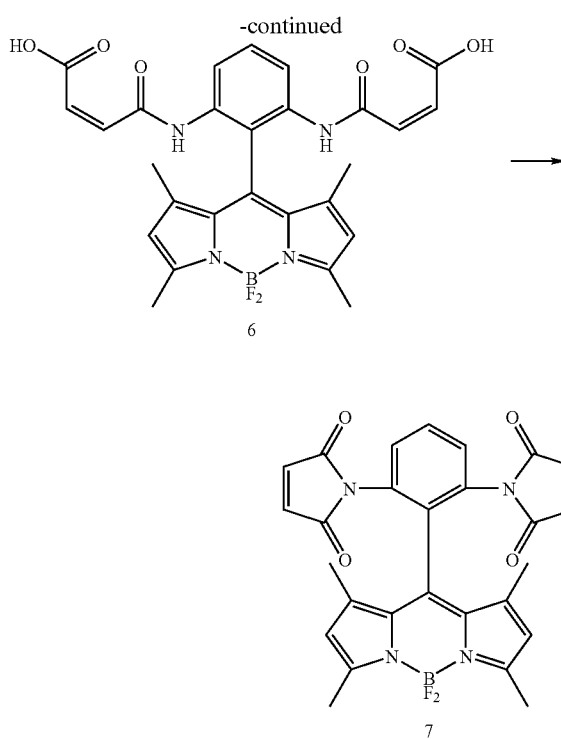

(a) Synthesis of Compound 5

2,6-Dinitrobenzaldehyde (0.78 g, 4.0 mmol) and 2,4-dimethylpyrrole (0.76 g, 8.0 mmol) were dissolved in 300 mL of dichloromethane. The solution was added with several drops of trifluoroacetic acid under an argon atmosphere, and the mixture was stirred at room temperature for 6 hours and 30 minutes with light shielding. Disappearance of the starting materials was confirmed by thin layer chromatography (developing solvent: dichloromethane, alumina), and then the reaction mixture was added with 150 mL of a solution of DDQ (1.0 g, 4.4 mmol) in dichloromethane. The reaction mixture was stirred at room temperature for 20 minutes, and then washed twice with water. The washed aqueous layer was extracted with dichloromethane, and the dichloromethane layer was combined with the original dichloromethane layer and dried over anhydrous magnesium sulfate. The organic layer was concentrated under reduced pressure, and then the residue was purified by alumina column chromatography (eluent: dichloromethane).

The resulting brown solid was dissolved in 30 mL of acetic acid, and added with 100 mL of concentrated hydrochloric acid and a solution obtained by dissolving 16 g of tin chloride dihydrate in 10 mL of water, and the mixture was stirred at 80° C. for 2 hours with light shielding. The reaction mixture was returned to room temperature, then neutralized with 10 N aqueous sodium hydroxide, and filtered by using a Buechner funnel. The filtrate was extracted with dichloromethane, and the solid separated by the filtration was sufficiently washed with dichloromethane. All the dichloromethane layers were combined, and dried over anhydrous magnesium sulfate. The organic layer was concentrated under reduced pressure, and the resulting brown solid was dissolved in 150 mL of toluene. The solution was added with 6 mL of DIEA, and further added with 6 mL of $BF_3$-$OEt_2$ under an argon atmosphere, and the mixture was stirred at room temperature for 30 minutes. After completion of the reaction, the reaction mixture was washed three times with water and once with saturated brine. The aqueous layer was extracted once with ethyl acetate, and all the organic layers were combined, and dried over anhydrous sodium sulfate. The organic layer was concentrated under reduced pressure, and then the residue was purified by silica gel column chromatography (eluent: dichloromethane) to obtain Compound 5 as red solid (52 mg, yield: 4%).

$^1$H NMR (300 MHz, $CDCl_3$) δ 1.74 (6H, s), 2.55 (6H, s), 3.59 (4H, br), 6.00 (2H, s), 6.19 (2H, d, J=7.9 Hz), 7.01 (1H, t, J=7.9 Hz).

MS (ESI+) 335, [M-F]+.

(b) Synthesis of Compound 6

Compound 5 (50 mg, 0.15 mmol) and maleic anhydride (30 mg, 0.33 mmol) were stirred in 30 mL of acetic acid at room temperature for 3 hours with light shielding. Disappearance of the starting materials was confirmed by thin layer chromatography (developing solvent: dichloromethane/methanol=19/1, silica gel), and the reaction mixture was concentrated under reduced pressure. The residue was suspended in chloroform, and the suspension was filtered through a glass filter of 3 G to obtain Compound 6 as orange solid (19 mg, yield: 23%).

$^1$H NMR (300 MHz, $CDCl_3$) δ 1.55 (6H, s), 2.48 (6H, s), 6.08 (2H, s), 6.22 (2H, d, J=12.6 Hz), 6.46 (2H, d, J=12.6 Hz), 7.72 (1H, t, J=7.0 Hz), 8.03 (2H, d, J=7.0 Hz).

MS (ESI$^-$) 549, [M–H]$^-$.

(b) Synthesis of Compound 7

Compound 6 (19 mg, 0.03 mmol) and sodium acetate (5 mg, 0.06 mmol) were added to 30 mL of acetic anhydride, and the mixture was stirred overnight at 80° C. with light shielding. Disappearance of the starting materials was confirmed by thin layer chromatography (developing solvent: dichloromethane, silica gel), and the reaction mixture was concentrated under reduced pressure. The residue was dissolved in dichloromethane and washed three times with water and once with saturated brine. The washed aqueous layer was extracted with dichloromethane, and the dichloromethane layer was combined with the original dichloromethane layer and dried over anhydrous magnesium sulfate. The organic layer was concentrated under reduced pressure, and then the residue was purified by silica gel column chromatography (eluent: dichloromethane) to obtain Compound 7 as orange solid (8.7 mg, yield: 50%).

$^1$H NMR (300 MHz, $CDCl_3$) δ 1.71 (6H, s), 2.46 (6H, s), 5.94 (2H, s), 6.67 (4H, s), 7.49 (2H, d, J=7.9 Hz), 7.74 (1H, t, J=7.9 Hz).

MS (ESI+) 515, [M+H]+.

Example 3

Synthesis of Michael Adducts of Compound 4

Compounds 8 to 10 were synthesized by the reaction of Michael addition of Compound 4 and acetone, butanone or cyclohexanone.

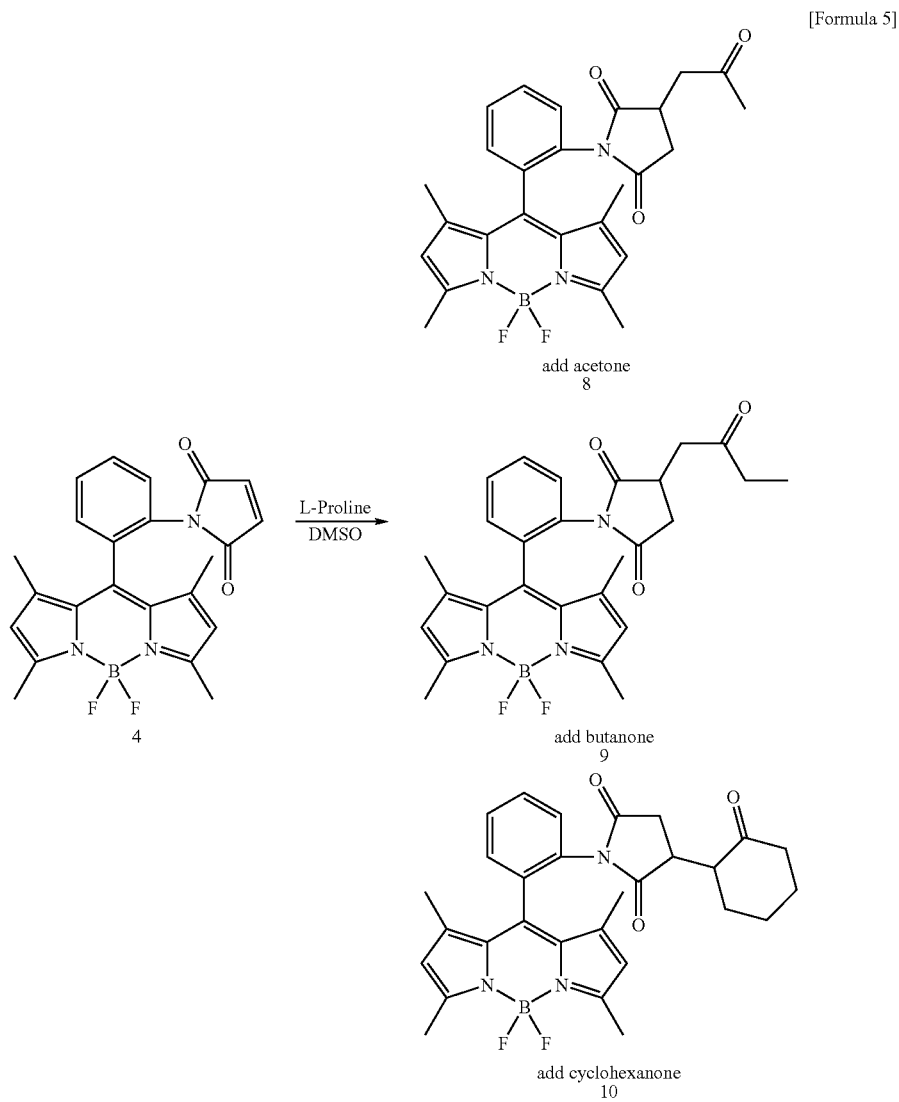

(a) Synthesis of Compound 8

Compound 4 (22 mg, 50 μmol) and L-proline (3 mg, 25 μmol) were dissolved in 0.5 mL of dimethyl sulfoxide. The solution was added with 1 mL of acetone, the reaction vial was sealed, and the reaction mixture was stirred at room temperature for three days with light shielding. The reaction mixture was diluted with 50 mL of dichloromethane, washed three times with water and once with saturated brine, and dried over anhydrous magnesium sulfate. The reaction mixture was concentrated under reduced pressure, and then the residue was purified by silica gel column chromatography (eluent: dichloromethane) to obtain Compound 8 as orange solid (12 mg, yield: 51%).

HRMS (ESI+) Calcd for [M-F]+, 472.2208, Found, 472.2248.

(b) Synthesis of Compound 9

Compound 4 (4.2 mg, 10 μmol) and L-proline (0.2 mg, 2 μmol) were dissolved in 0.5 mL of dimethyl sulfoxide. The solution was added with 1.5 mL of butanone, the reaction vial was sealed, and the mixture was stirred at room temperature for four days with light shielding. The reaction mixture was diluted with 50 mL of dichloromethane, washed three times with water and once with saturated brine, and dried over anhydrous magnesium sulfate. The reaction mixture was concentrated under reduced pressure, and then the residue was purified by silica gel column chromatography (eluent: dichloromethane) to obtain Compound 9 as orange solid (1.4 mg, yield: 33%).

HRMS (ESI+) Calcd for [M-F]+, 498.2364, Found, 498.2357.

(b) Synthesis of Compound 10

Compound 4 (4.2 mg, 10 μmol) and L-proline (0.2 mg, 2 μmol) were dissolved in 0.5 mL of dimethyl sulfoxide. The solution was added with 1.5 mL of cyclohexanone, the reaction vial was sealed, and the mixture was stirred at room temperature for four days with light shielding. The reaction mixture was diluted with 50 mL of dichloromethane, washed three times with water and once with saturated brine, and dried over anhydrous magnesium sulfate. The reaction mixture was concentrated under reduced pressure, and then the residue was purified by silica gel column chromatography (eluent: dichloromethane) to obtain Compound 10 as orange oil (88 mg).

HRMS (ESI+) Calcd for [M+Na]+, 500.1933, Found, 500.1940.

Example 4

Fluorescence Quantum Yields of Michael Adducts of Compound 4

Fluorescence quantum yields of Compounds 8, 9 and 10 synthesized by the reaction of Michael addition and Compound 4 were measured in various solvents by using a fluorescence spectrophotometer, F-4500, manufactured by Hitachi, Ltd. The pH of $H_2O$ (pH 7.4) was adjusted with a sodium phosphate buffer (0.1 mol/L). On the basis of the fluorescence quantum yield of fluorescein in 0.1 mol/L aqueous sodium hydroxide defined to be 0.85, fluorescence quantum yields in each solvent were calculated. The results are shown in Table 1. Compound 4 gave a low fluorescence quantum yield of 0.062 or lower in each solvent, and only slightly emitted fluorescence. On the other hand, Compounds 8, 9 and 10 gave high fluorescence quantum yields of 0.6 or higher, and emitted extremely intense fluorescence. Therefore, it was confirmed that Compound 4 of the present invention, which was substantially non-fluorescent, gave Michael adducts emitting intense fluorescence as a result of the reaction of Michael addition with the nucleophilic agents, regardless of the type of the reaction solvent.

TABLE 1

|  | Solvent | | | |
| --- | --- | --- | --- | --- |
|  | 8 Add acetone | 9 Add butanone | 10 Add cyclohexanone | Compound 4 |
| $H_2O$ (pH 7.4) | 0.602 | 0.601 | 0.716 | 0.005 |
| DMSO | 0.678 | 0.743 | 0.687 | 0.003 |
| $CH_3CN$ | 0.693 | 0.644 | 0.747 | 0.003 |
| DMF | 0.694 | 0.660 | 0.717 | 0.004 |
| MeOH | 0.715 | 0.615 | 0.722 | 0.002 |
| Acetone | 0.748 | 0.672 | 0.726 | 0.002 |
| $CH_2Cl_2$ | 0.792 | 0.736 | 0.735 | 0.002 |
| $CHCl_3$ | 0.835 | 0.770 | 0.793 | 0.003 |
| Benzene | 0.827 | 0.782 | 0.755 | 0.003 |
| Cyclohexane | 0.837 | 0.764 | 0.761 | 0.055 |
| Hexane | 0.838 | 0.732 | 0.743 | 0.062 |

Example 5

High Throughput Screening for Michael Addition Reaction Catalyst and Solvent

With the following reaction conditions, high throughput screening for catalyst and solvent of the reaction of Michael addition of Compound 4 and acetone was performed.

Solvent: 2.7 mL

Catalyst: 0.02 mmol/L

Compound 4: 0.1 mmol/L

Acetone: 0.3 mL

Reaction time: 24 hours

Figure 2:
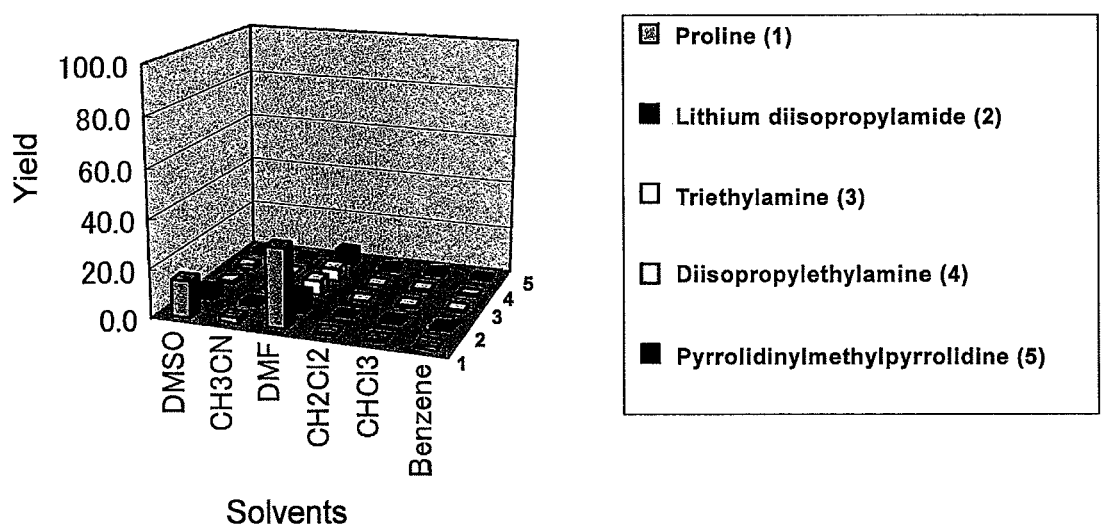
FIG. 2 Graph showing the results of high throughput screening for catalysts and solvents for the reaction of Michael addition (Example 5).

The reaction was carried out at room temperature in a sealed vial. After completion of the reaction, the reaction mixture was diluted 10 times with dimethyl sulfoxide, and fluorescence intensity was measured by using a fluorescence spectrophotometer, LS50B (Perkin Elmer, excitation wavelength: 505 nm, fluorescence wavelength: 525 nm). The resulting fluorescence intensity was converted into a reaction yield on the basis of the calibration curve of FIG. 1 which was obtained by measuring fluorescence intensity of composition of the compounds in dimethyl sulfoxide at each yield (namely, composition of Compound 4 and Compound 8 at each yield). The results are shown in FIG. 2. It was confirmed that reaction yields in the reaction of Michael addition using various catalysts and solvents were obtainable only by measurement of fluorescence intensity, and the reaction conditions of the reaction of Michael addition including catalyst, solvent and the like were successfully screened efficiently by using Compound 4 of the present invention.

Example 6

Reaction of Compound 7 and Compounds Having Thiol Group

Figure 3:
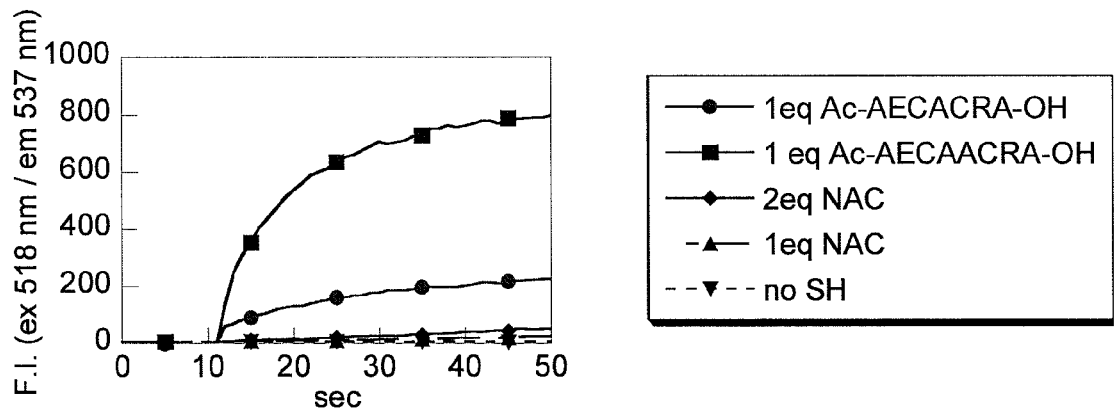
FIG. 3 Graph showing the results of the reaction of Compound 7 of the present invention and compounds having a cysteine residue.

In a fluorescence cell for 3-mL volume, 3 μL of a 1 mmol/L solution of Compound 7 in DMSO was diluted with 3 mL of a 0.1 mol/L sodium phosphate buffer (pH=7.4) to prepare a 1 μmol/L solution of Compound 7 (final concentration of DMSO: 0.1%). By using a fluorescence spectrophotometer, F-4500, manufactured by Hitachi, Ltd., set at a temperature of 37° C., excitation wavelength of 518 nm and fluorescence wavelength of 537 nm, measurement of fluorescence intensity was started. At 10 seconds after the start of the measurement, 3 μL (1 equivalent) or 6 μL (2 equivalents) of 1 mmol/L N-acetylcysteine (NAC), Ac-AECACRA-OH or Ac-AECAACRA-OH peptide (having acetyl group (Ac) at the N-terminus, carboxy group at the C-terminus, and amino acid residues are indicated with one-letter codes) in 0.1% TFA aqueous solution was added, and the fluorescence intensity was measured up to 40 seconds after the addition (50 seconds after the start of the measurement). The results are shown in FIG. 3. Almost no increase of fluorescence intensity was observed with addition of 2 equivalents of NAC having one thiol group to Compound 7, whilst significant increase of fluorescence intensity was observed when Ac-AECACRA-OH or Ac-AECAACRA-OH peptide having two thiol groups in a single molecule was added. It was thus demonstrated that by using Compound 7 of the present invention, a fluorescence tag excitable with visible light was successfully incorporated with high selectivity into a peptide, a protein or the like having two adjacent cysteine residues in a single molecule.

Example 7

High Throughput Screening for Michael Addition Reaction Catalyst and Solvent (2)

The number of type of catalyst was increased from that of the experiment of Example 5 to perform high throughput screening for catalyst and solvent of the reaction of Michael addition between Compound 4 and acetone.

Solvent: 2.7 mL

Catalyst: 0.02 mmol/L

Compound 4: 0.1 mmol/L

Acetone: 0.3 mL

Reaction time: 24 hours

Figure 4:
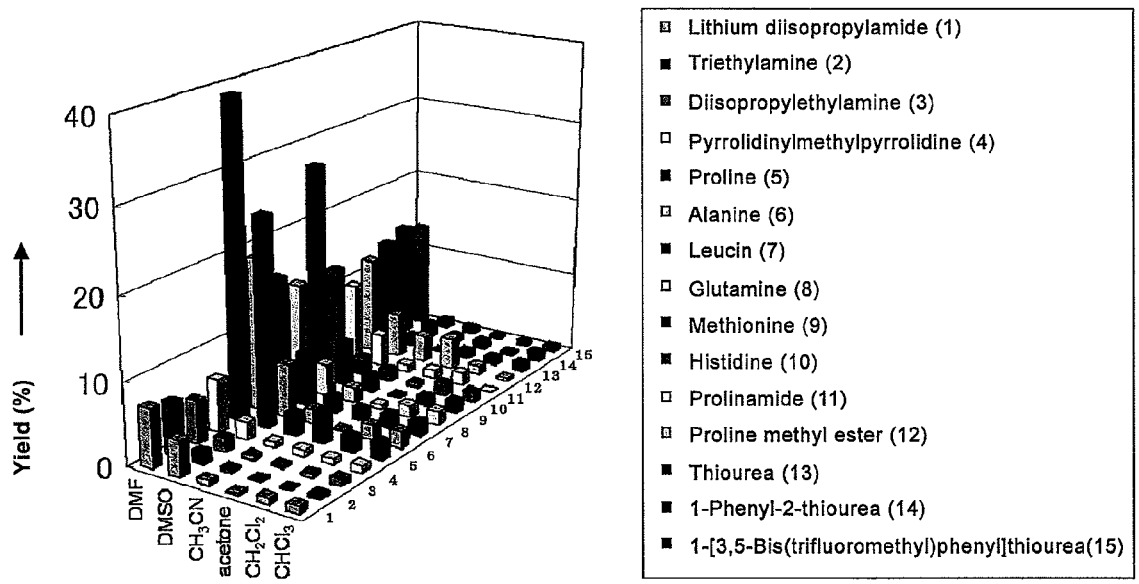
FIG. 4 Graph showing the results of high throughput screening for catalysts and solvents for the reaction of Michael addition (Example 7).

In the same manner as that of Example 5, the reaction was carried out at a room temperature in a sealed vial. After completion of the reaction, the reaction mixture was diluted 10 times with dimethyl sulfoxide, and fluorescence intensity was measured by using a fluorescence spectrophotometer, LS50B (Perkin Elmer, excitation wavelength: 505 nm, fluorescence wavelength: 525 nm). The resulting fluorescence intensity was converted into a reaction yield on the basis of the calibration curve of FIG. 1 which was obtained by measuring fluorescence intensity of composition of the compounds in dimethyl sulfoxide at each yield (namely, composition of Compound 4 and Compound 8 at each yield). As shown by the results indicated in FIG. 4, when the solvent was dimethylformamide and the catalyst was proline, the highest reaction yield was observed, and the next highest reaction yields followed when the solvent was dimethylformamide and the catalyst was methionine, and also when the solvent was dimethyl sulfoxide and the catalyst was proline. It was confirmed that reaction yields in the reaction of Michael addition using more various types of catalysts and solvents, as compared with Example 5, were obtainable only by measurement of fluorescence intensity, and the various reaction conditions of Michael addition including catalyst, solvent and the like were successfully screened efficiently by using Compound 4 of the present invention.

Example 8

Detailed Monitoring of Conditions Chosen by High Throughput Screening

Figure 5:
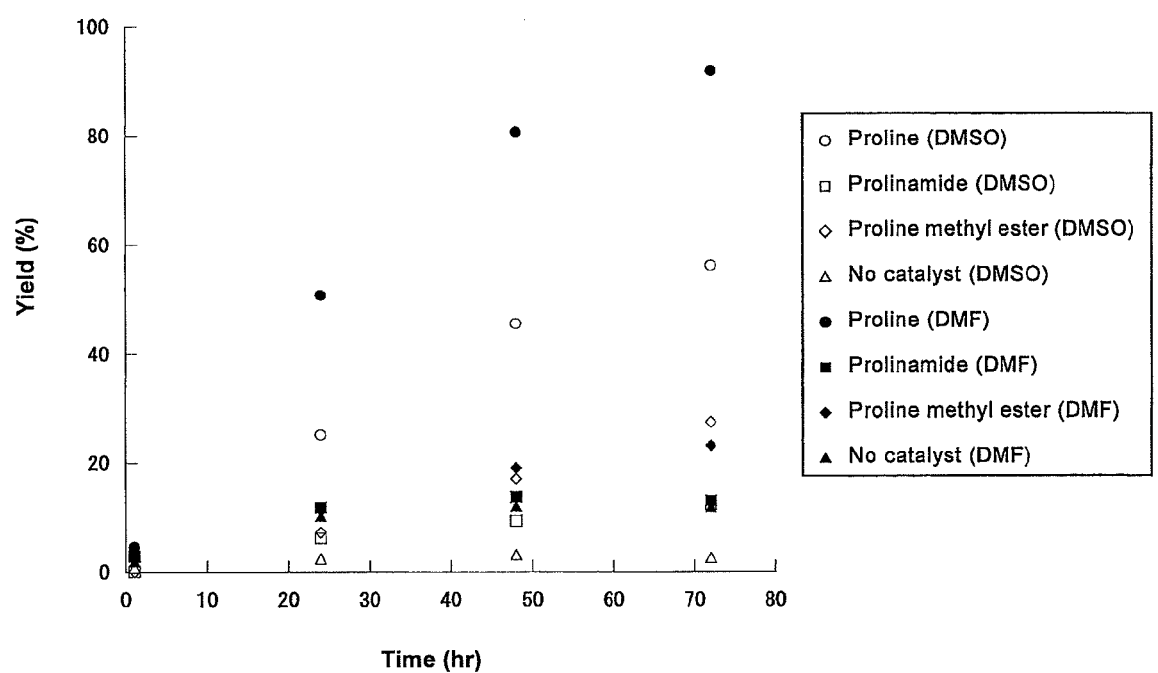
FIG. 5 Graph showing the results of detailed monitoring of the conditions chosen by high throughput screening (Example 8).

By using proline, which gave relatively higher yields in the experiments of Examples 5 and 7, or derivatives thereof as a catalyst, and dimethylformamide or dimethyl sulfoxide as a solvent, advance of the chemical reaction performed under the same conditions as those of Example 7 was monitored with changing reaction time to be 0, 24, 48 and 72 hours. The results are shown in FIG. 5.

It was confirmed that changes of reaction yield of Michael addition over period of time were successfully monitored by measurement of fluorescence intensity using Compound 4 of the present invention.

Example 9

Synthesis of Michael Adduct of Compound 4 (2) (Synthesis of Compound 11)

Compound 11 was synthesized by the reaction of Michael addition of Compound 4 and NAC.

[Formula 6]

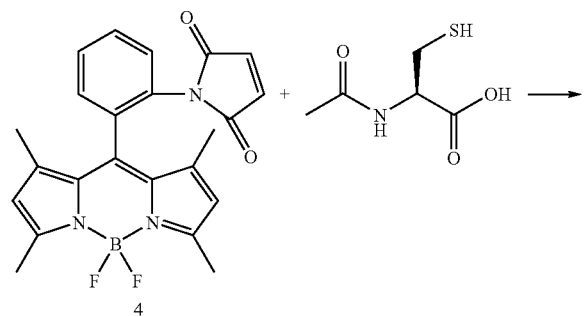

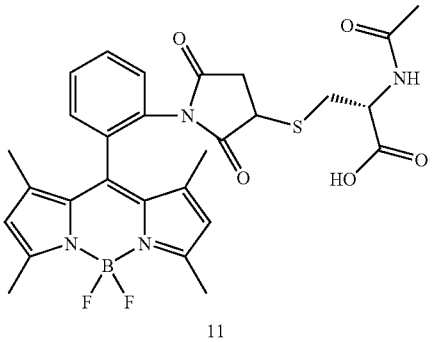

Compound 4 (7 mg, 17 μmol) was dissolved in 1 mL of dimethyl sulfoxide. NAC (16 mg, 0.1 mmol) was added to the solution, the reaction vial was sealed, and the mixture was stirred at room temperature for 1 hour with light shielding. The reaction mixture was diluted with 50 mL of dichloromethane, washed three times with water and once with saturated brine, and dried over anhydrous magnesium sulfate. The reaction mixture was concentrated under reduced pressure, and then the residue was purified by preparative silica gel chromatography (developing solvent: dichloromethane) to obtain Compound 11 as orange solid (7.5 mg, yield: 76%).

HRMS (ESI-) Calcd for [M-H]-, 581.1842, Found, 581.1877.

Example 10

Confirmation of Influence of pH on Compounds 4 and 11

Fluorescence quantum yields of Compounds 4 and 11 in a 0.1 mol/L sodium phosphate buffer (pH 2.1, 3.1, 4.1, 5.1, 6.0, 7.0, 7.4, 7.9 or 8.8) were measured by using a fluorescence spectrophotometer, F-4500, manufactured by Hitachi, Ltd. On the basis of the fluorescence quantum yield of fluorescein in 0.1 mol/L aqueous sodium hydroxide defined to be 0.85, fluorescence quantum yields in each buffer were calculated. The results are shown in Table 2. Compound 4 of the present invention, which was substantially non-fluorescent, gave a reaction product, i.e., Compound 11, which emitted intense fluorescence, as a result of the reaction with NAC which is a compound having thiol group, and thus it was confirmed that fluorescence intensities of Compound 4 and the reaction product, Compound 11, were not affected by pH.

TABLE 2

|  | Compound 4 before reaction | Compound 11 after reaction |
| --- | --- | --- |
| pH 2.1 | <0.01 | 0.73 |
| pH 3.1 | <0.01 | 0.69 |
| pH 4.1 | <0.01 | 0.84 |
| pH 5.1 | <0.01 | 0.74 |
| pH 6.0 | <0.01 | 0.75 |
| pH 7.0 | <0.01 | 0.83 |
| pH 7.4 | <0.01 | 0.73 |
| pH 7.9 | <0.01 | 0.61 |
| pH 8.8 | 0.02 | 0.72 |

Example 10

Reaction of Compound 4 and Compounds Having Thiol Group

Figure 6:
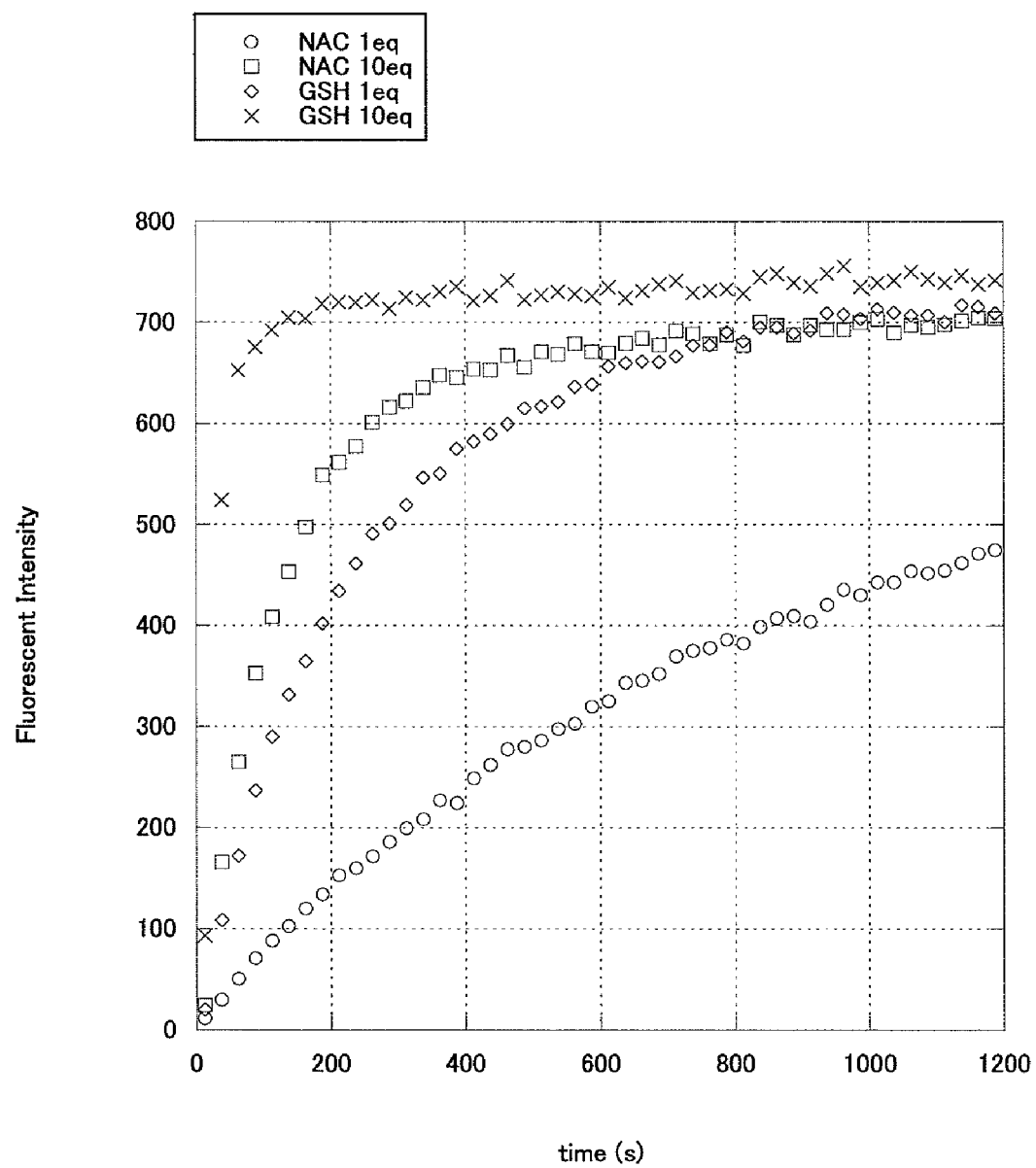
FIG. 6 Graph showing the results of the reaction of Compound 4 of the present invention and compounds having a thiol group.

In a fluorescence cell for 3-mL volume, 3 μL of a 1 mmol/L solution of Compound 4 in dimethyl sulfoxide was diluted with 3 mL of a 0.1 mol/L sodium phosphate buffer (pH=7.4) to prepare a 1 μmol/L solution of Compound 4 (final concentration of dimethyl sulfoxide: 0.1%). By using a fluorescence spectrophotometer, F-4500, manufactured by Hitachi, Ltd., set at room temperature, excitation wavelength of 505 nm, and fluorescence wavelength of 520 nm, the measurement of fluorescence intensity was started. At 10 seconds after the start of the measurement, 3 μL of a 1 mmol/L or 10 mmol/L solution of NAC or reduced glutathione (GSH) in dimethyl sulfoxide was added, and the fluorescence intensity was measured up to 1190 seconds after the addition (1,200 seconds after the start of the measurement). The results are shown in FIG. 6.

Figure 7:
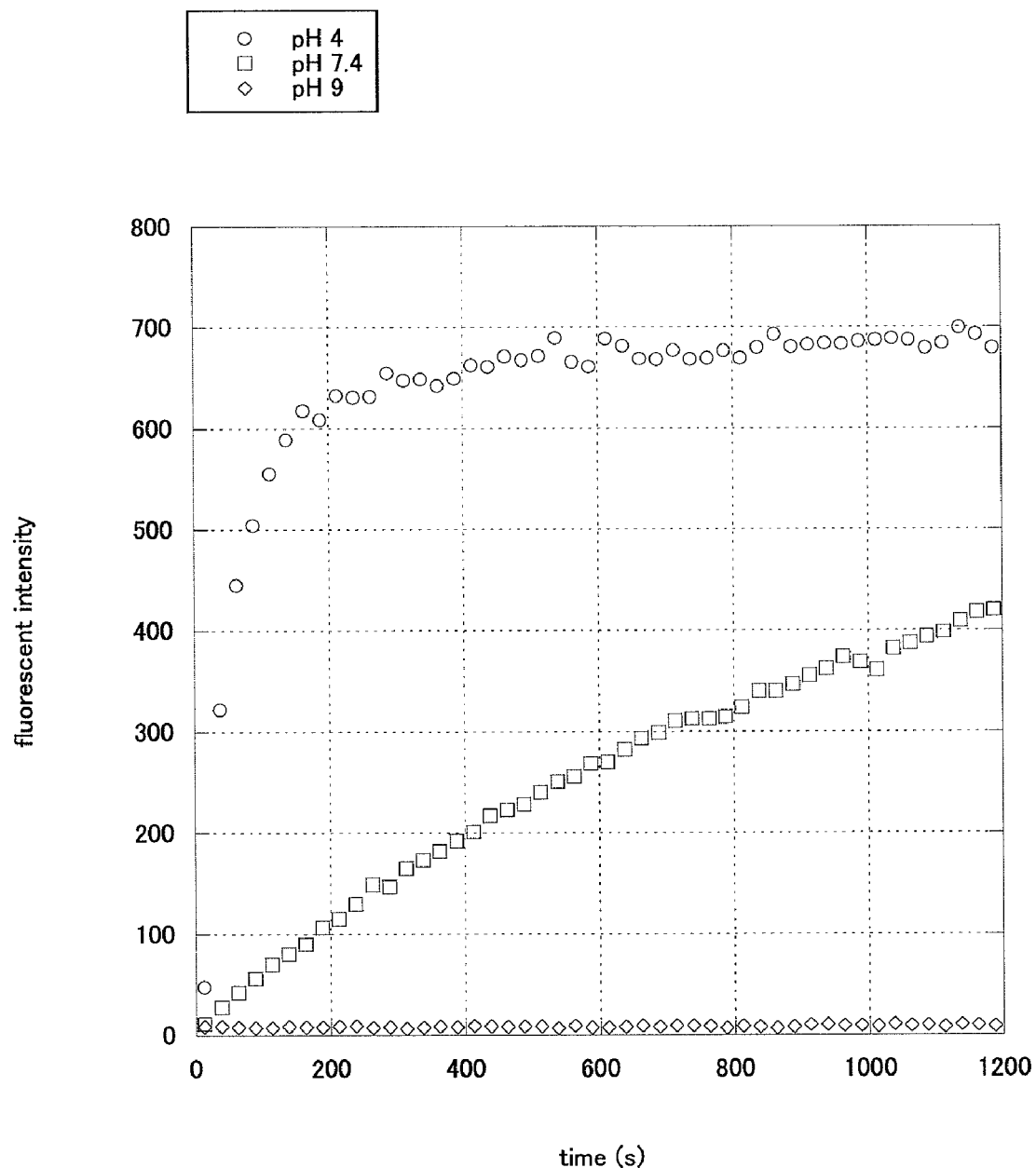
FIG. 7 Graph showing the results of the reaction of Compound 4 of the present invention and compounds having a thiol group.

Further, the experiment of adding 1 mmol/L NAC was also performed in sodium phosphate buffers of pH 4 and pH 9. The results are shown in FIG. 7. It was demonstrated that by using Compound 4 of the present invention, a fluorescence tag excitable with visible light was successfully incorporated into a compound having thiol group such as NAC and GSH.

INDUSTRIAL APPLICABILITY

The compound represented by the aforementioned general formula (I) or a salt thereof of the present invention has a property of being per se substantially non-fluorescent, and giving a fluorescent Michael adduct as a product of the reaction of Michael addition. By using the compound or a salt thereof of the present invention, a chemical substance having applicability as a catalyst in the reaction of Michael addition can be efficiently screened, and optimum reaction conditions can be conveniently chosen in a short time. The compound or a salt thereof of the present invention has high reactivity to thiol group of cysteine residue, and accordingly, is capable of achieving efficient fluorescence-labeling of a peptide, a protein or the like containing a cysteine residue.

What is claimed is:

1. A compound represented by the following general formula (I):

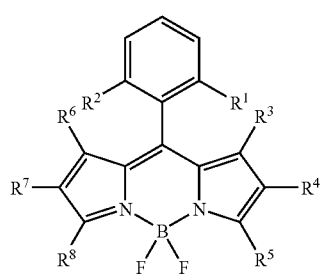

(I)

wherein $R^1$ and $R^2$ independently represent hydrogen atom, or a group represented by the following formula (A):

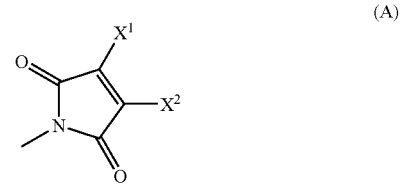

(A)

wherein $X^1$ and $X^2$ independently represent hydrogen atom, a $C_{1-6}$ alkyl group which may have a substituent, a $C_{1-6}$ alkoxy group which may have a substituent, or a halogen atom, provided that at least one of $R^1$ and $R^2$ represented by formula (A); $R^3$ and $R^6$ independently represent a $C_{1-6}$ alkyl group which may have a substituent; $R^4$ and $R^7$ independently represent hydrogen atom, a $C_{1-6}$ alkyl group which may have a substituent, carboxy group, a $C_{1-6}$ alkoxycarbonyl group, or sulfo group, or $R^4$ may combine with $R^3$ to form a condensed aryl ring together with two carbon atoms to which they bond, wherein the aryl ring may have a substituent, and/or $R^7$ may combine with $R^6$ to form a condensed aryl ring together with two carbon atoms to which they bond, wherein the aryl ring may have a substituent; and $R^5$ and $R^8$ independently represent a $C_{1-6}$ alkyl group which may have a substituent, an aryl group which may have a substituent, a $C_{1-6}$ alkoxycarbonyl group which may have a substituent, a vinyl group which may have a substituent, a thienyl group which may have a substituent, or a pyrrolyl group which may have a substituent, or a salt thereof.

2. The compound according to claim 1 or a salt thereof, wherein $R^1$ is a group represented by formula (A), $R^2$ is hydrogen atom, and $X^1$ and $X^2$ are hydrogen atoms.

3. The compound according to claim 1 or a salt thereof, wherein $R^1$ and $R^2$ independently represent a group represented by formula (A), and $X^1$ and $X^2$ are hydrogen atoms.

4. The compound or a salt thereof according to claim 1, which is for searching a reaction system of the reaction of Michael addition.

5. The compound or a salt thereof according to claim 1, which is for labeling of an amino acid, a peptide, or a protein which has a cysteine residue.

* * * * *